(12) United States Patent
Woo

(10) Patent No.: US 7,575,592 B2
(45) Date of Patent: Aug. 18, 2009

(54) SYNTHETIC BLOOD VESSEL GRAFTS

(75) Inventor: Yi-Ren Woo, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 345 days.

(21) Appl. No.: 11/542,735

(22) Filed: Oct. 3, 2006

(65) Prior Publication Data

US 2008/0082161 A1   Apr. 3, 2008

(51) Int. Cl.
*A61F 2/06*   (2006.01)

(52) U.S. Cl. .................................................. 623/1.26

(58) Field of Classification Search ........ 623/1.11–2.18
See application file for complete search history.

(56) References Cited

U.S. PATENT DOCUMENTS

| | | | | |
|---|---|---|---|---|
| 4,670,286 | A * | 6/1987 | Nyilas et al. ............... | 427/2.24 |
| 4,911,713 | A | 3/1990 | Sauvage et al. | |
| 5,891,195 | A * | 4/1999 | Klostermeyer et al. ..... | 623/1.26 |
| 6,299,638 | B1 * | 10/2001 | Sauter ........................ | 623/1.26 |
| 6,652,543 | B2 * | 11/2003 | Spence et al. ............... | 606/153 |
| 2002/0095210 | A1 * | 7/2002 | Finnegan et al. ........... | 623/3.26 |
| 2003/0171802 | A1 * | 9/2003 | Wilder et al. .............. | 623/1.24 |
| 2004/0024452 | A1 * | 2/2004 | Kruse et al. ................ | 623/2.13 |
| 2005/0228487 | A1 * | 10/2005 | Kujawski .................... | 623/1.26 |
| 2005/0267559 | A1 | 12/2005 | DeOliveira | |
| 2006/0025855 | A1 * | 2/2006 | Lashinski et al. ............ | 623/2.1 |
| 2006/0064119 | A9 * | 3/2006 | Tilson et al. ................. | 606/153 |
| 2006/0085060 | A1 * | 4/2006 | Campbell ................... | 623/1.26 |
| 2007/0154515 | A1 * | 7/2007 | Johnson et al. ............. | 424/423 |

FOREIGN PATENT DOCUMENTS

| | | |
|---|---|---|
| EP | 0955019 A2 | 11/1999 |
| WO | WO 2006/013234 A1 | 2/2006 |

OTHER PUBLICATIONS

A. Albertini et al., "Modified Bentall Operation: The Double Sewing Ring Technique," European Journal of Cardio-Thoracic Surgery 32 (2007) 804-806.

* cited by examiner

*Primary Examiner*—Suzette J Gherbi
(74) *Attorney, Agent, or Firm*—Lerner, David, Littenberg, Krumholz & Mentlik, LLP

(57) ABSTRACT

A synthetic blood vessel graft (e.g., for use with a prosthetic heart valve) includes a mounting cuff adjacent at least one end for facilitating attachment of the graft to another structure (e.g., a sewing cuff of a heart valve). The mounting cuff may be sized and shaped to provide good conformance to the target structure to which it may be attached (e.g., the heart valve sewing cuff). The graft is preferably preclotted. Especially for use with a tissue valve (which must be supplied in a packaging solution that would react with a preclotting agent), the graft is preferably supplied separately from the valve.

15 Claims, 5 Drawing Sheets

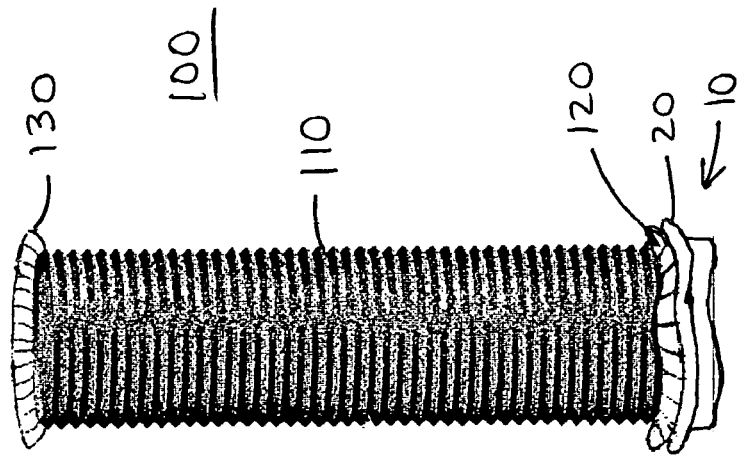
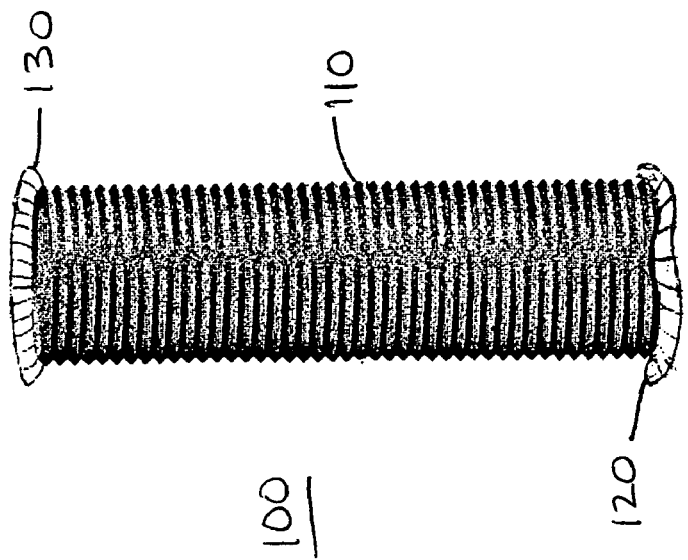

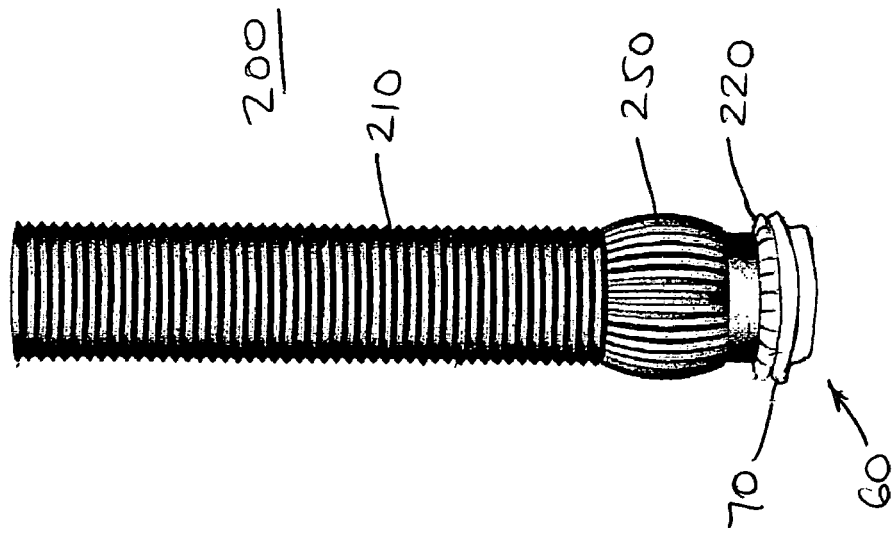
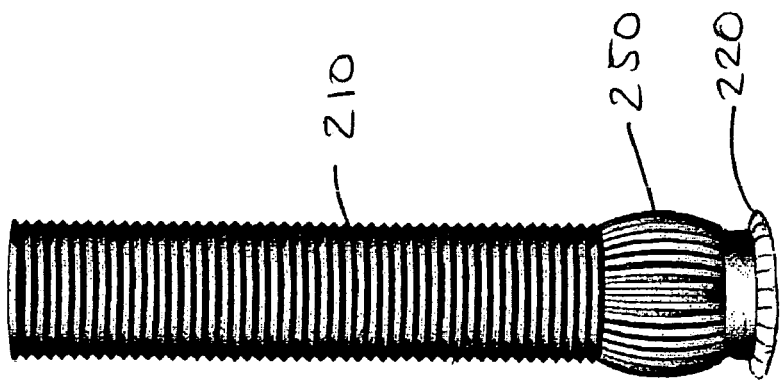

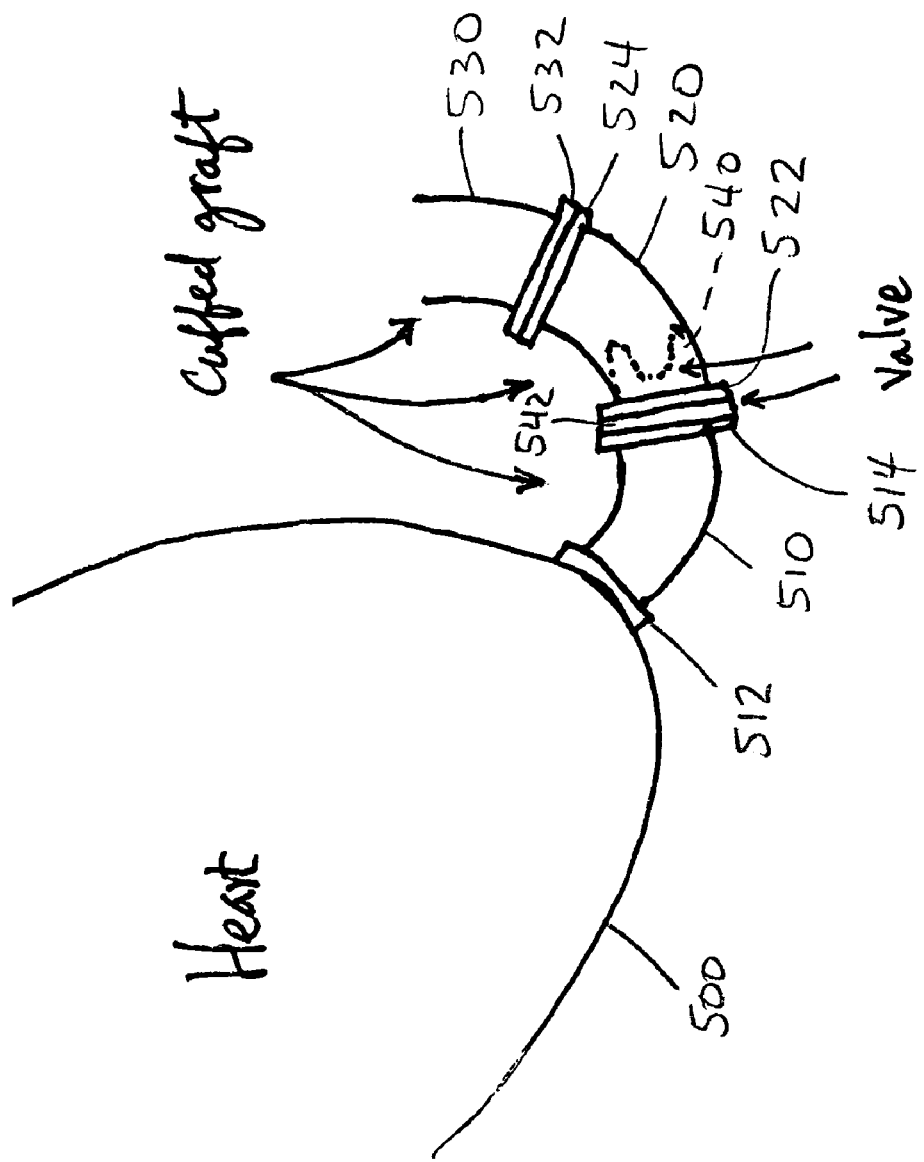

SYNTHETIC BLOOD VESSEL GRAFTS

BACKGROUND OF THE INVENTION

This invention relates to synthetic blood vessel grafts. Although the invention also has other possible uses, the invention is particularly useful in conjunction with artificial heart valves.

The use of a composite valved graft is an established treatment for patients with aortic valve disease and ascending aortic aneurysms. It is preferred to have the graft part of the composite device supplied "preclotted" or pre-sealed. Having a pre-sealed graft not only eliminates the need for preclotting during surgery, it also tends to reduce the possibility of post-implantation bleeding, because the manufacturing process for pre-sealing can be carried out more consistently to reliably provide an adequate seal. The material used to seal the graft is hydrolysable, so that after implantation the sealant will be degraded and removed to allow the host tissue to grow into the graft to stabilize it and to cover the graft to form an ideal blood-contacting surface.

Because of the benefits of a preclotted graft, most mechanical valved grafts that are commercially available today are supplied with the graft pre-sealed. However, for a composite device that includes a valve made of tissue, the graft is not preclotted because the valve needs to be stored in a solution to prevent the tissue from dehydration. The material that would be used to preseal the graft portion of the device would react undesirably with the packaging solution. Therefore, for a Bentall procedure (replacement of aortic valve and adjacent section of the aorta) using a tissue valve, the surgeon has to either seal the graft portion of a composite device using the patient's blood, or construct a composite device using a tissue valve and a preclotted graft that are supplied separately. For the latter case, the available preclotted grafts are basically straight tubes that need to be carefully attached to the tissue valve to provide a structurally stable interface and adequately prevent blood leakage.

In view of the foregoing, it is an object of this invention to provide improved preclotted synthetic grafts, especially for use in conjunction with artificial heart valves, and most especially with tissue heart valves.

SUMMARY OF THE INVENTION

This and other objects of the invention are accomplished in accordance with the invention by providing a preclotted graft with a mounting cuff on at least one end of the graft. The mounting cuff can be used to more easily attach the graft to an artificial heart valve (e.g., a tissue valve) to form a leak-tight interface. The mounting cuff can also include features to facilitate quicker and more reliable attachment to an artificial heart valve, especially when the graft is to be used with a specific valve. Such a graft can be used with a tissue valve to more easily form a composite device for a Bentall procedure. Or the graft can be used with a mechanical valve when a composite device with the desired mechanical valve is not available. The mounting cuff(s) on the graft can also be designed for other applications where there is a need to attach the graft to another device, component, or portion of the patient's anatomy to ease the attachment process and enhance the attachment integrity.

Further features of the invention, its nature and various advantages, will be more apparent form the accompanying drawings and the following detailed description.

BRIEF DESCRIPTION OF THE DRAWINGS

FIG. 3 is a simplified perspective view of an illustrative embodiment of a synthetic graft in accordance with the invention.

FIG. 4 is similar to FIG. 3, but shows the graft associated with an illustrative prosthetic heart valve in accordance with the invention.

FIG. 5 is a simplified perspective view of another illustrative embodiment of a synthetic graft in accordance with the invention.

FIG. 6 is similar to FIG. 5, but shows the graft associated with an illustrative prosthetic heart valve in accordance with the invention.

FIG. 9 is a simplified elevational view showing an illustrative implant that includes multiple synthetic grafts in accordance with the invention.

DETAILED DESCRIPTION

Figure 2:
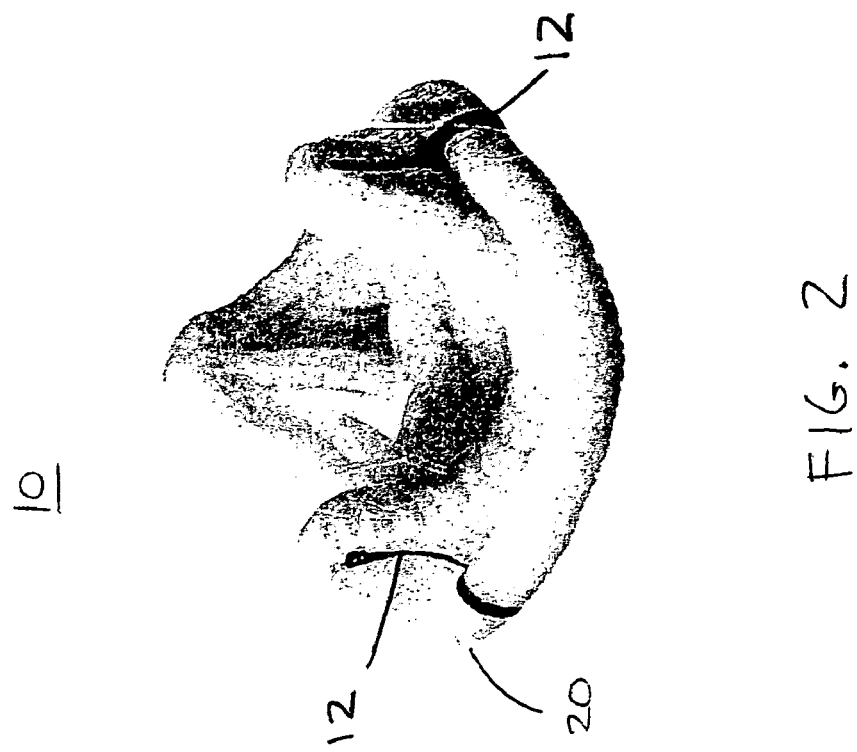
FIG. 2 is another view of the valve shown in FIG. 1.
Figure 1:
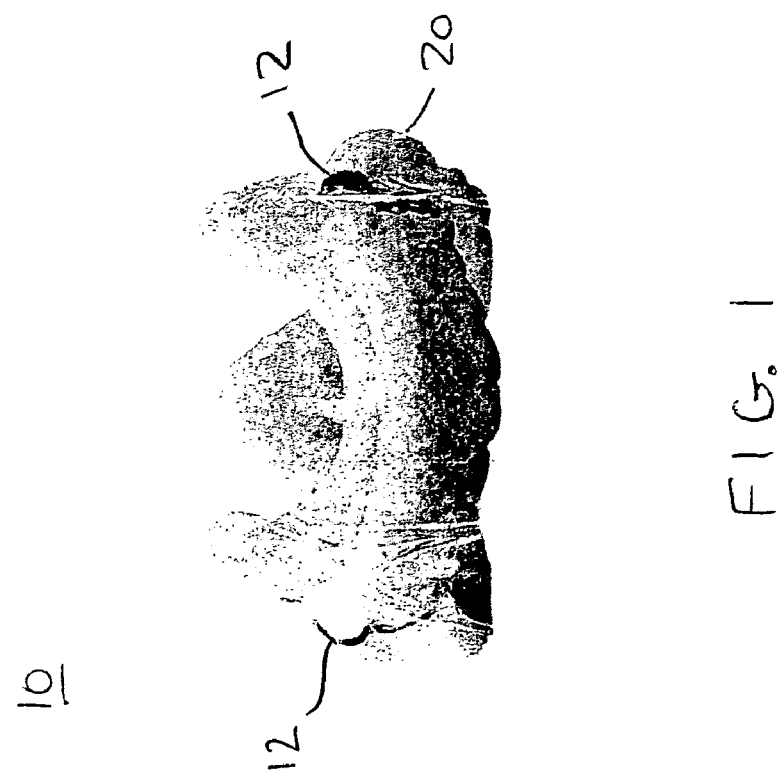
FIG. 1 is a simplified elevational view of an illustrative prosthetic, artificial heart valve that can be used with a synthetic graft in accordance with the invention.

An illustrative prosthetic, artificial heart valve 10 that can be used with a synthetic graft in accordance with the invention is shown in FIGS. 1 and 2. Valve 10 is a tissue valve with a sewing cuff 20 around the outside of the valve. Sewing cuff 20 extends radially outward from the remainder of the valve, and it also extends annularly all the way around the valve. Unlike most of the remainder of the valve, sewing cuff 20 is typically made of synthetic material rather than tissue. For example, sewing cuff 20 may include an outer layer of knitted or woven dacron fabric or other similar material. The remaining radially outer surface of valve 10 may also be covered with such fabric. But the inner, actually operating portions of valve 10 are tissue. Sewing cuff 20 is used for suturing the valve into the patient. For example, sutures (not shown) are typically passed through sewing cuff 20 into adjacent living tissue of the patient (e.g., the annulus of the patient's heart valve that remains after the native heart valve leaflets have been excised).

It will be noted that sewing cuff 20 is scalloped, i.e., it rises adjacent each of the three commissure posts of the valve (radially inside the dark marks 12 on valve 10), and it falls between each adjacent pair of commissures. This may be done so that the cuff 20 will more closely follow the patient's native valve annulus, which is also typically scalloped in this same general way.

FIG. 3 shows a first illustrative embodiment of a synthetic graft 100 in accordance with the invention. Graft 100 is basically a hollow tube 110 with a first mounting cuff 120 at one end and a second mounting cuff 130 at the other end. Graft 100 may basically be made of woven or knitted, biocompatible fabric such as dacron. Each of cuffs 120 and 130 may also include such fabric. Each cuff may be given additional bulk by forming a roll of the fabric, by enclosing another body such as a biocompatible string in an outer layer of the fabric, or by any other suitable means. Each mounting cuff 120 and 130 preferably extends annularly all the way around the adjacent end of the tube 110, and each cuff 120 and 130 also preferably extends radially outward from the adjacent portion of the tube.

Graft 100 is intended for use with valve 10. Accordingly, the end of graft 100 adjacent to mounting cuff 120 is sized and shaped to fit around the outside of the portion of valve 10 that is above sewing cuff 20 in FIGS. 1 and 2. FIG. 4 shows valve 10 and graft 100 after they have been put together in this way. Mounting cuff 120 is scalloped in the same way that sewing cuff 20 is scalloped. Accordingly, mounting cuff 120 closely follows sewing cuff 20 all the way around combined structures 10 and 100. The two cuffs 20 and 120 may be similar in size, i.e., they may be at similar radial distance from a longitudinal axis which passes centrally through assembled elements 10 and 100. In addition, cuffs 20 and 120 may have the same basic scalloped shape (i.e., the same number and size of scallops in the same general locations) so that when cuffs 20 and 120 are put together as shown in FIG. 4, they are congruent to one another or abut one another all the way around the assembly of elements 10 and 100.

If desired, elements 10 and 100 can be sutured together in the condition shown in FIG. 4 to produce a composite device. This can be done, for example, with sutures that are passed through and between both of cuffs 20 and 120. The resulting composite device can then be sutured into a patient, e.g., by passing more sutures through cuffs 20 and 120 and adjacent tissue of the patient. Alternatively, valve 10 can first be sutured into the patient separately, e.g., by passing sutures through sewing cuff 20 and adjacent tissue of the patient. Thereafter, graft 100 can be added, e.g., by passing additional sutures through cuff 120 and at least cuff 20. In either case, the other end of graft 100 is ultimately attached to another portion of the patient's anatomy (e.g., healthy aorta tissue) using cuff 130 (e.g., by passing additional sutures through cuff 130 and adjacent native tissue). In whatever way that elements 10 and 100 are used together, the congruency of cuffs 20 and 120 facilitates putting them together in a secure and blood-tight implant.

FIG. 5 shows another illustrative embodiment of a synthetic graft 200 in accordance with the invention. Once again, graft 200 is basically a hollow tube 210. In this embodiment, however, the graft has a mounting cuff 220 at only one of its ends. The other end is basically straight, i.e., without a cuff. Closely adjacent to cuff 220, graft 200 bulges radially outwardly as shown at 250.

In the embodiment shown in FIG. 5 mounting cuff 220 is basically straight (i.e., it is not scalloped like mounting cuff 120 in FIGS. 3 and 4). Accordingly, graft 200 is adapted for use with a valve that has a straight cuff. FIG. 6 shows how graft 200 may be put together with a valve 60 having a straight cuff 70. FIG. 6 is generally similar to FIG. 4, except that in FIG. 6 cuffs 70 are 220 are both straight. Again, because both cuffs 70 and 220 have the same basic size and shape, they are congruent to one another when elements 60 and 200 are put together as shown in FIG. 6. This basic congruency of cuffs 70 and 220 means that they closely follow one another all the way around an assembly of elements 60 and 200. Once again, this facilitates secure and blood-tight implantation of elements 60 and 200 together. As in the case of the earlier embodiment, elements 60 and 200 can first be put together as a composite device, which is then implanted. Or valve 60 can first be implanted, and then element 200 can be added over the implanted valve. With either approach, the other (uncuffed) end of graft 200 (remote from cuff 220) is ultimately connected to other tissue of the patient (e.g., healthy aorta tissue).

Because the grafts (e.g., 100, 200) of this invention can be supplied separately from valves (e.g., 10, 60) with which they may be used, the grafts of this invention can be supplied preclotted regardless of the type of valve with which they may be used. Any suitable preclotting substance (e.g., collagen or gelatin) can be used. The preclotting can be part of the process of manufacturing the graft. In this way very high-quality (i.e., gap- and defect-free) preclotting can be achieved. Then the preclotted graft can be packaged and stored for later use. For example, typical packaging for such a preclotted graft is sterile and dry, so that there is nothing to react with and degrade the preclotting agent during what may be a prolonged period of storage prior to use. When it is desired to use the graft (e.g., with a tissue valve), the graft is removed from its packaging and for the first time associated with the valve. Just prior to such association, the valve has typically been removed from its separate packaging. Thus the valve (assumed in this example to be a tissue valve) can be stored wet in a packaging solution. Because the graft is not associated with the valve until the valve is out of its packaging solution, this avoids any possible adverse effect of the valve packaging solution on the graft (especially the preclotting of the graft).

Although the example immediately above assumes use of a graft of this invention with a tissue valve, the grafts of this invention are equally usable with mechanical valves. For example, when a composite device with a desired mechanical valve is not available, an initially separate graft in accordance with this invention can be put together with that desired mechanical valve. Similarly, the mounting cuffs (e.g., 120, 130, 220) on grafts in accordance with the invention can be designed (e.g., shaped and/or sized) for other applications and placed on the graft at any location where there is a need to attach the graft to another device, component, or portion of the patient's anatomy. Among the benefits of such a purpose-designed mounting cuff is that it eases the attachment process and enhances the attachment integrity.

Figure 8:
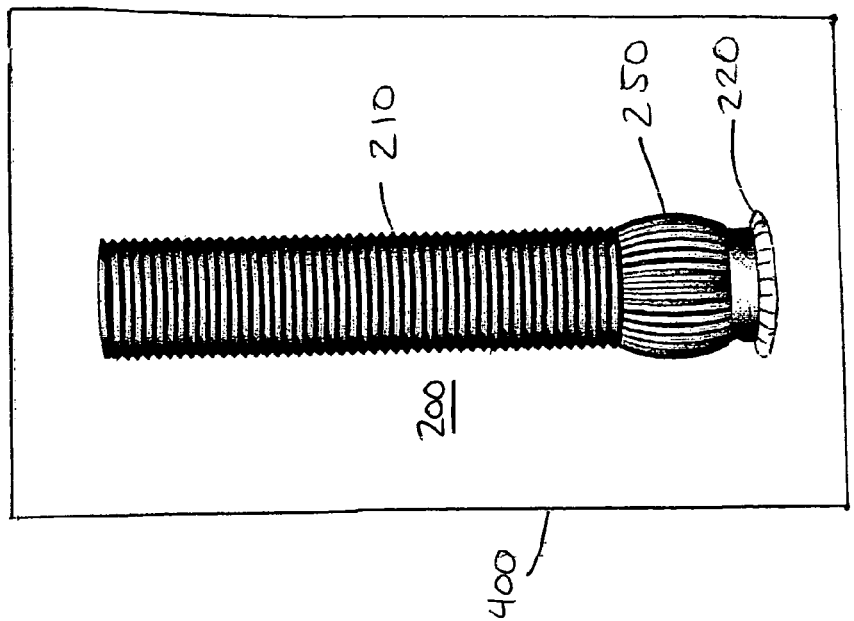
FIG. 8 is a simplified depiction of the FIG. 5 graft in an illustrative storage container in accordance with the invention.
Figure 7:
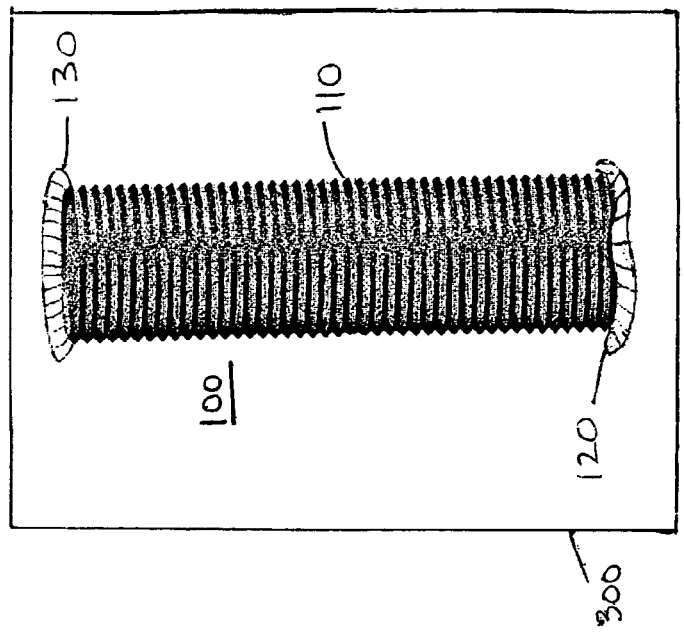
FIG. 7 is a simplified depiction of the FIG. 3 graft in an illustrative storage container in accordance with the invention.

FIGS. 7 and 8 illustrate the point that the grafts of this invention (e.g., 100, 200) may be stored and supplied to a surgeon for use in storage containers or packages 300 or 400. Containers 300/400 preferably enclose the graft and keep it sterile until it is ready to be used by a surgeon. Then the surgeon opens the container 300/400, removes the graft (e.g., 100 or 200), and uses it (e.g., in association with a prosthetic heart valve) as described earlier in this specification. The graft is preferably already preclotted when it is initially placed in the container as part of the graft manufacturing process. The environment in the container is preferably such as to have no adverse effect on the preclotting or the preclotting agent during what may be relatively long storage time. Note that no valve is present in the storage container (300 or 400) with the graft. Any valve is preferably supplied separately (e.g., in a separate container, which can hold the valve in a different environment than is used for the graft).

FIG. 9 shows an example of use of instances of synthetic blood vessel grafts in accordance with the invention. In FIG. 9 a first synthetic graft 510 has mounting cuffs 512 and 514 adjacent its respective opposite axial ends. Synthetic graft 520 has mounting cuffs 522 and 524 adjacent its respective opposite axial ends. Synthetic graft 530 has mounting cuff 532 adjacent at least one of its axial ends.

The assembly shown in FIG. 9 is an apico-aortic conduit that connects the apex of the heart to the descending aorta. In use, the surgeon cuts a hole in the apex of the heart and connects the proximal end 512 of the valved graft to the opening. The distal end of the device (not shown) can be either cuffed or uncuffed and is attached to healthy aorta tissue.

Graft 510 is attached to heart 500 using mounting cuff 512. Prosthetic valve 540 (e.g., similar to any of the previously described prosthetic valves and having sewing cuff 542) is connected between grafts 510 and 520. In particular, the sewing cuff 542 of valve 540 is sandwiched between the mounting cuffs 514 and 522 of grafts 510 and 520, respectively. The actual operating (leaflet) portion of valve 540 is inside graft 520 near mounting cuff 522. Graft 530 is attached to the end of graft 520 that is remote from valve 540. In particular, mounting cuffs 524 and 532 are used to make this attachment. As has already been said, the distal end of graft 530, which is not shown and which can be either cuffed or uncuffed, is attached to healthy aorta tissue of the patient. The valved graft assembly shown in FIG. 9 provides a low-resistance bypass for the blood in the ventricle to go out to supply the body.

FIG. 9 further illustrates the point that a synthetic graft in accordance with the invention can be intended for use in a specific anatomical location in a patient. For that purpose the graft can be sized and shaped to mate with features of the patient's anatomy at or adjacent to that location. For example, one or both mounting cuffs of the graft can be sized and shaped for congruence with anatomical features of the patient. As just one illustration of this in the context of FIG. 9, mounting cuff 512 can be sized and shaped for congruence with heart tissue.

It will be understood that the foregoing is only illustrative of the principles of the invention, and that various modifications can be made by those skilled in the art without departing from the scope and spirit of the invention. For example, the particular type of tissue valve 10 shown in FIGS. 1 and 2 is only one of many different types of tissue and mechanical valves with which the grafts of this invention can be used. References herein to artificial heart valves or to prosthetic heart valves are not intended to limit the structures thus mentioned to valves that are necessarily used in the heart. Some such valves may be used adjacent to the heart or otherwise in aid of the functioning of the heart. For example, FIG. 9 shows such a valve 540 at a location that is somewhat spaced from heart 500 per se. As another example of modifications within the scope of the invention, alternatives to the suturing mentioned herein are well known and can be used if desired. Examples of such alternatives are staples, hooks, and the like. The invention is not limited to straight grafts. Rather, the invention can be applied to grafts having many different configurations such as Y-shaped grafts and grafts with a central portion from which one or more side branches extend. A mounting cuff in accordance with this invention can be provided adjacent an otherwise free end of any one or more tubular portions of such non-straight grafts.

The invention claimed is:

1. A synthetic blood vessel graft comprising:
   a tubular member; and
   a mounting cuff adjacent an end of the tubular member, wherein:
      the graft is intended for use with a prosthetic heart valve that includes a sewing cuff;
      the mounting cuff is sized and shaped for congruence with the sewing cuff; and
      the sewing cuff is scalloped and the mounting cuff is similarly scalloped.

2. The synthetic graft defined in claim 1 wherein the mounting cuff extends radially outwardly from the tubular member.

3. The synthetic graft defined in claim 2 wherein the mounting cuff extends annularly all the way around the tubular member.

4. The synthetic graft defined in claim 1 wherein at least the tubular member is preclotted.

5. A method of using a synthetic blood vessel graft with a prosthetic heart valve comprising:
   supplying the heart valve in a first storage container;
   supplying the graft in a separate, second storage container, the graft having a mounting cuff adjacent one of its ends;
   removing the heart valve from the first container;
   removing the graft from the second container; and
   using the mounting cuff to associate the graft with the heart valve, wherein the using comprises suturing the graft and the heart valve together employing sutures through the mounting cuff.

6. The method defined in claim 5 wherein the heart valve includes a sewing cuff, and wherein the using further comprises:
   positioning the mounting cuff and the sewing cuff adjacent to one another.

7. The method defined in claim 6 wherein the using further comprises:
   suturing through the sewing cuff and the mounting cuff to secure those cuffs to one another.

8. The method defined in claim 5 further comprising:
   suturing the heart valve into a patient prior to the using.

9. The method defined in claim 5 further comprising:
   suturing the heart valve and the graft into a patient after the using.

10. The method defined in claim 5 wherein the graft is already preclotted when it is in the second storage container.

11. The method defined in claim 5 wherein the heart valve comprises tissue, and wherein the first container contains a packaging solution in which the heart valve is stored.

12. A synthetic blood vessel graft product for use with a prosthetic heart valve that includes tissue and a sewing cuff comprising:
   a synthetic blood vessel graft structure including a tubular member and a mounting cuff adjacent an end of the tubular member; and
   a storage container for containing the graft structure separate from the prosthetic heart valve, wherein:
      the mounting cuff is sized and shaped to abut the sewing cuff after the graft structure has been removed from the storage container; and
      the sewing cuff is scalloped and the mounting cuff is similarly scalloped.

13. The product defined in claim 12 wherein the storage container maintains the graft structure in a sterile condition.

14. The product defined in claim 12 wherein the graft structure is already preclotted in the storage container.

15. The product defined in claim 12 wherein the mounting cuff is adapted for sutures to pass through it after the graft structure has been removed from the storage container.

* * * * *